(12) United States Patent
Scheinman et al.

(10) Patent No.: US 7,702,068 B2
(45) Date of Patent: Apr. 20, 2010

(54) CONTRABAND DETECTION SYSTEMS AND METHODS

(75) Inventors: Elan D. Scheinman, Redwood City, CA (US); Michael Ellenbogen, Wayland, MA (US); Richard Robehr Bijjani, Westford, MA (US)

(73) Assignee: Reveal Imaging Technologies, Inc., Bedford, MA (US)

( * ) Notice: Subject to any disclaimer, the term of this patent is extended or adjusted under 35 U.S.C. 154(b) by 0 days.

(21) Appl. No.: 10/588,138

(22) PCT Filed: Feb. 11, 2005

(86) PCT No.: PCT/US2005/004675

§ 371 (c)(1),
(2), (4) Date: Feb. 12, 2007

(87) PCT Pub. No.: WO2005/095931

PCT Pub. Date: Oct. 13, 2005

(65) Prior Publication Data

US 2007/0147586 A1    Jun. 28, 2007

Related U.S. Application Data

(60) Provisional application No. 60/543,768, filed on Feb. 11, 2004.

(51) Int. Cl.
*G01N 23/04* (2006.01)

(52) U.S. Cl. ............................. 378/57; 378/4; 378/901
(58) Field of Classification Search ............. 378/4–20, 378/57, 91, 98, 901; 382/132, 131

See application file for complete search history.

(56) References Cited

U.S. PATENT DOCUMENTS

| | | | | |
|---|---|---|---|---|
| 4,247,774 | A | 1/1981 | Brooks | 250/367 |
| 4,315,157 | A | 2/1982 | Barnes | 250/445 T |
| 5,367,552 | A * | 11/1994 | Peschmann | 378/57 |
| 5,570,403 | A | 10/1996 | Yamazaki et al. | 378/5 |
| 5,583,903 | A | 12/1996 | Saito et al. | 378/19 |
| 5,661,774 | A | 8/1997 | Gordon et al. | 378/101 |
| 5,692,029 | A | 11/1997 | Husseiny et al. | 378/88 |
| 6,185,272 | B1 | 2/2001 | Hiraoglu et al. | 378/57 |
| 6,218,943 | B1 | 4/2001 | Ellenbogen | 340/572.4 |
| 2002/0176531 | A1 | 11/2002 | McClelland et al. | 378/57 |

FOREIGN PATENT DOCUMENTS

| | | |
|---|---|---|
| EP | 0 471 455 A2 | 2/1992 |
| EP | 0 816 873 A1 | 1/1998 |
| EP | 0 825 457 A2 | 2/1998 |
| WO | 96/13839 | 5/1996 |
| WO | 97/18462 | 5/1997 |
| WO | 03/029844 A2 | 4/2003 |

* cited by examiner

*Primary Examiner*—Jurie Yun
(74) *Attorney, Agent, or Firm*—T. J. Clark; Mintz, Levin, Cohn, Ferris, Glovsky and Popeo, P.C.

(57) ABSTRACT

In one embodiment, the present invention provides a CT scanner system for use in baggage screening at security checkpoints.

1 Claim, 17 Drawing Sheets

CONTRABAND DETECTION SYSTEMS AND METHODS

BACKGROUND OF THE INVENTION

1. Field of the Invention

The present invention relates to baggage inspection systems. More particularly, it relates to container, e.g., baggage, inspection systems and methods for detecting security threats.

2. Discussion of Related Art

Security checkpoints, such as those located in airports, screen people and packages for contraband, such as weapons or explosives. Various technologies are used at such checkpoints. Typically, individuals pass through metal detection devices. Projection x-ray systems screen baggage and packages. In current conditions of heightened security, passengers can experience long delays in passing through security checkpoints. For baggage, an operator typically reviews all images of screened baggage to determine whether the baggage includes contraband. A typical operator receives extensive training to recognize certain types of objects in an x-ray image. Furthermore, a typical operator receives training to distinguish objects layered within the bags from a single two dimensional x-ray image.

Projection x-ray systems were designed to provide high-resolution images for the detection of guns and knives. Despite such imaging, the individuals using conventional projection x-ray systems to perform screening in certain circumstances do not detect forbidden objects. Specifically, projection x-ray scanners are not designed to detect explosives. Therefore, it is difficult for even the most highly trained screener to detect explosives using projection x-ray technology. There is currently no mandate to use explosive detection systems (EDS) to screen carry-on baggage. However, a need remains for a system that can detect explosives in carry-on baggage, especially for carry-on baggage of selected individuals (e.g., Computer Assisted Passenger Profiling System (CAPPS) selectees).

In addition to individuals and carry-on baggage, checked bags are also now scanned at airports. Generally, in the United States, the Transportation Security Administration (TSA) uses computed tomography (CT) scanning for checked bags. CT scanners create a three dimensional image of a bag which allows better differentiation of objects relative to projection x-ray systems. Explosive detection system designers specifically developed and deployed CT scanners for the detection of explosives. Conventional CT scanners do not provide a high-resolution dual energy projection x-ray image useful for detecting weapons. For this reason among others, the TSA has not used CT scanners for carry-on baggage or security checkpoints.

As noted above, CT technology is effective for explosive detection. CT machines typically incorporate a rotating ring or "gantry" on which the X-ray source and detectors are mounted. FIG. 1 is a cross sectional view of a conventional CT scanner 10. The CT scanner 10 includes a gantry 11 surrounding a tunnel 20. A conveyor (not shown) moves baggage through the tunnel 20 for scanning. The gantry 11 rotates about the tunnel, producing one slice of data for each rotation. An x-ray source 30 produces a narrow angle beam 40. A detector 31 is positioned on the gantry 11 to intersect the x-ray beam 40 passing through the tunnel. The detector 31 may consist of multiple detectors, which typically are located equal distances from the x-ray source. The x-ray source 30 and detector 31 must be sized and positioned so that the entire tunnel falls within the x-ray beam. The data from the detector is analyzed using a computer to generate a three-dimensional representation of the contents of the baggage being scanned.

Conventional CT scanning and reconstruction used in baggage inspection is slow and cumbersome. There are two known methods for CT scanning, i.e., helical and start/stop. In helical scanning, an object under inspection, e.g., a bag, is continuously moved through the scanner. The bag has to be moved slowly so that each rotation of the gantry is substantially in a single plane. In start/stop scanning, the bag is periodically stopped and a single slice is scanned. The bag is then moved a short distance, stopped and scanned again. Both of these processes result in slow movement of baggage through the scanner. Once the data has been collected, the data is reconstructed to create a three dimensional representation of the baggage. From the three dimensional representation, individual items are reviewed as possible threats. The three dimensional representation, or slices of it, may also be displayed for review by an operator.

A need remains for systems and methods that provide a higher throughput relative to conventional CT systems.

Furthermore, The TSA has recognized the need to improve the security process at the passenger checkpoint, as evidenced by a recent TSA request for proposals for checkpoint EDS. Simply replacing the existing checkpoint X-ray systems with EDS will be an expensive proposition. It is currently driven by the need to improve the detection performance at the checkpoint. Adding additional benefits such as increased throughput and labor reduction will provide incentive for other stakeholders to support the capital investment.

Adding special selectee lanes to existing passenger checkpoints would help with throughput but limits the ability of TSA or an airport to respond to changes in the threat condition or an increase in the percentage of CAPPS selectees. In addition, forcing only selected passengers to the selectee lane alerts any potential terrorist of his or her status while also alerting the traveling public to their special selectee status. This alert can cause additional problems for TSA based on perceived discriminatory practices.

TSA and airports are struggling to keep up with passenger loads using today's passenger screening systems and procedures. Lines up to 2 hours can form during peak periods and will likely get worse as TSA headcount is further rationalized and passenger loads increase. Adding additional screening lanes can cost millions and take months. Airlines and airports would eagerly embrace a system that can significantly increase the throughput of the passenger checkpoint as a means to improve passenger service while maintaining or increasing detection performance.

SUMMARY OF THE INVENTION

In one embodiment, the present invention provides a CT scanner system for use in baggage screening at security checkpoints. According to one aspect of the invention, the CT scanner system processes x-ray data to locate and eliminate non-contraband without full CT reconstruction of the entire bag. For example, one embodiment of the CT scanner system disqualifies objects of insufficient size, density, or mass as potential threats. According to another aspect of the invention, the CT scanner system performs CT reconstruction of non-eliminated objects to determine whether any of the non-eliminated objects qualify as a potential threat. According to another aspect of the invention, the CT scanner system processes the data to locate weapons or explosives without operator review. According to another embodiment, a stationery x-ray projection image, whether generated from the CT scanner X-ray source in a parked position, or by a separate fixed view x-ray scanner in front of or after the CT scanner, can be used to automatically eliminate or exclude potential threats from objects under inspection.

One embodiment of the invention provides a method for scanning a container to determine if the container poses a threat. The method includes: performing a CT scan of the container to produce CT scan data; processing the CT scan data to create lineogram data; determining a measured value for a characteristic of a first object in the container based on the lineogram data; comparing the measured value to a predetermined value; and if the measured value has a specified relationship to the predetermined value then determining that the object does not pose a threat.

Another embodiment of the invention provides a system for scanning a container to determine if the container poses a threat. The system includes: a CT scanner having a rotating gantry; a conveyor for advancing containers through the CT scanner; a host processor in communication with the CT scanner, the host processor operative to receive data from the CT scanner; and a detection processor in communication with the host processor. The detection processor receives CT data from the CT scanner and processes the CT data to create lineogram data, determines a measured value for a characteristic of a first object in the container based on the lineogram data, compares the measured value to a predetermined value, and if the measured value has a specified relationship to the predetermined value, then determines that the object does not pose a threat.

In another embodiment, the present invention provides a high throughput, high security checkpoint screening system. An adaptive system that inspects passenger baggage based on security intelligence inputs, such as CAPPS, can provide high throughput with improved security. Compared to today's carry-on inspection process, a carry-on EDS according to the present invention can improve security and double passenger throughput, with reduced screener labor.

Deployment of EDS at checkpoints can improve the overall detection performance of the passenger screening process, and eliminate the need for redundant hand searching of selectee bags.

According to one embodiment of the invention, a CT scanner incorporates an x-ray source and a detector array that are placed on a rotating disk (the "gantry"). The gantry spins at a specified speed, e.g., 60 RPM, during an automated EDS scan. If the disk is stopped, projection X-ray images similar to the images generated by today's checkpoint x-ray machines can be generated.

According to one embodiment of a method according to the invention, all non-selectee passenger bags are inspected using a standard projection image, similar to today's carry-on screening process. For a normal passenger, the CT gantry is stopped and a projection image of a bag is created. In order to support the high resolution imaging used by a CT scanner during EDS scans, the imaging electronics acquire data significantly faster than today's conventional checkpoint scanners. This increased data acquisition speed allows this embodiment of the invention to speed up the conveyor belt, without sacrificing image quality. Therefore the inspection throughput for normal passenger bags can be more than three times the throughput of a conventional carry-on X-ray system.

In one embodiment, for CAPPS selectee passengers, the "greeter" helping passengers divest before they place bags on the belt simply indicates to the system (e.g., via a button) that a selectee passenger bag is approaching the system. In a specified period of time, e.g., less than 5 seconds, the CT gantry automatically starts spinning and the EDS system inspects the selectee bag using fully automated EDS techniques. Once the selectee bag is scanned and analyzed, a process that takes a specified time, e.g., approximately 20 seconds, the gantry stops again for normal bag inspection. This entire process can be completely transparent to the passenger. The process described here can eliminate the need for separate screeners for selectee bag hand search.

Thus, one embodiment of the invention provides a method for scanning a bag to determine if the bag poses a threat. The method includes: providing a CT scanner system; determining if a passenger is a selectee; if the passenger is not a selectee, then inspecting a bag associated with the passenger by using the CT scanner system to obtain a standard projection image data; and if the passenger is a selectee, then inspecting a bag associated with the passenger by using the CT scanner system to obtain CT data. The projection image generated by the CT scanner can be a stationary image or a "twisted" projection scan created using a slowly moving gantry.

Yet another embodiment of the invention provides a system that maintains a database of characteristics (e.g., the diameter) of a number (e.g., hundreds) of gun barrels and when the system detects a barrel shaped object, the system searches the database for a match. More specifically and with reference to FIG. 18, in one embodiment, a method according to one embodiment of the invention acquires and reconstructs a SnapScan or CT slice. The method analyzes the CT or SnapScan slice data to determine if a hollow circular or oval shape of a known diameter exists, the circular or oval shape being surrounded by metal or dense plastic. The method determines whether a hollow space is found. If not, the method determines if the method has analyzed the last slice for the container, e.g., bag, under inspection. If not, then the method goes to the next slice. If so, the method concludes that no gun was found in the container.

If a hollow space is found, the method determines if the hollow space is round, oval, or long rectangular. If so, the method determines whether the hollow shape matches any barrel diameters in a look up table of gun diameters. If so, the method determines whether the hollow is circular or oval shaped.

If the hollow is not circular or oval shaped, the method determines whether the object is long and straight enough and does not change diameter to qualify as a gun barrel according to a look up table of gun barrel characteristics. If the hollow is circular or oval shaped, the system inspects multiple adjacent slices and creates a 3D object and then determines whether the object is long and straight enough and does not change diameter to qualify as a gun barrel according to a look up table of gun barrel characteristics.

If the object does not qualify as a gun barrel, the method proceeds to determine if the last slice of the object has been analyzed. However, if the object does qualify as a gun barrel, the method marks the object as suspect for farther processing.

Still another embodiment provides a scanner system that utilizes a visible light camera to image each bag as it crosses a predetermined point outside or inside the scanner tunnel. The image can then be used by the scanner CPU to automatically identify features of the bag and/or to alter the scan speed to optimize throughput and detection. In another embodiment, the image can be used to associate passenger bags with scanner data and with automated decisions. In another embodiment, the visible light image can be used to help a screener identify the location of a suspect object in a passenger's bags. Another embodiment incorporates dynamic high resolution slowing and speeding up of the belt based on "on the fly" analysis. Since in one embodiment of the invention analysis of a bag proceeds simultaneously with scanning, an alarm can be addressed while the bag is still in the scanner. If analysis of the data indicates a potential threat for which it is not desirable to pursue resolution through data modification and reconstruction, the bag can be immediately subjected to a high-resolution scan. A high-resolution scan can be achieved by slowing down the gantry or the conveyor belt. A high-resolution image can be created and presented to an operator for review. If the gantry is slowed to about 10 RPM and the bag moves at a high speed of about 1.5 m/sec, a high-resolution line projection image can be obtained and presented to the operator with an overlay of the threat position. Alternatively, if the conveyor belt is slowed to about 1 cm/sec, a full 3D image of the bag using standard helical CT algorithms can be generated and presented to the operator.

DETAILED DESCRIPTION

Figure 2:
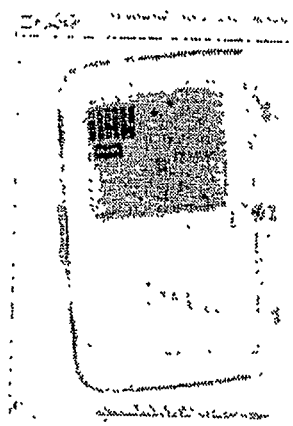
FIG. 2 is a representative image from a projection x-ray system.

The present invention relates to baggage inspection systems. FIG. 2 illustrates an image of a bag from a projection x-ray system such as a conventional system used at security checkpoints in airports. The objects in the bag overlap each other in the image. A highly trained operator must review each image to determine whether the bag includes contraband, such as weapons, explosives, or other excluded items. If the objects cannot be clearly viewed, the bag must be hand searched.

Figure 1:
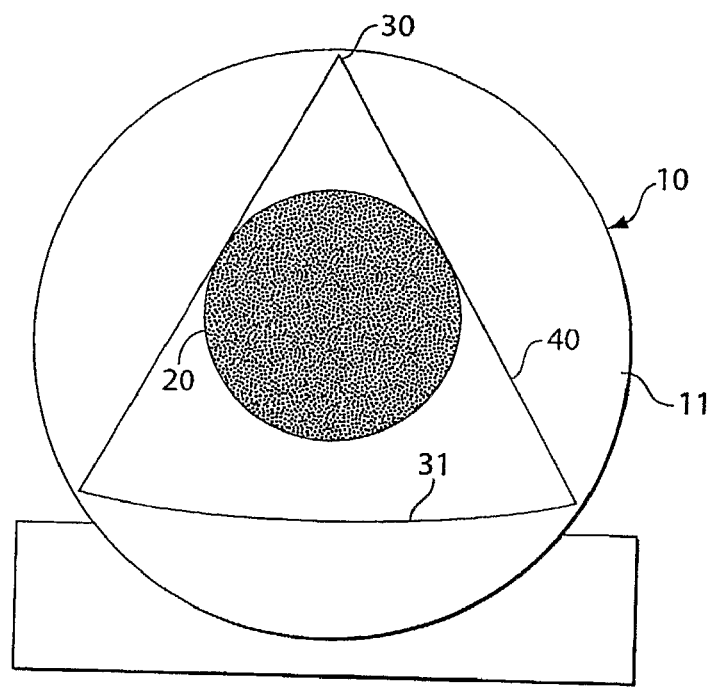
FIG. 1 is a cross sectional view of a conventional CT scanner which can be used with one embodiment of a processing system of the present invention.

One embodiment of a system according to the invention includes a CT scanner that obtains CT data of a container, e.g., a bag. CT data may be obtained from a CT scanner of any known design. For example, the CT data may be obtained from a conventional CT scanner as shown in FIG. 1 and discussed above. In another embodiment, a system according to the invention can include a different CT scanner configuration such as that disclosed in U.S. patent application Ser. No. 10/677,967, entitled "Folded Array CT Baggage Scanner", filed on Oct. 2, 2003, and incorporated herein by reference in its entirety. FIG. 8 illustrates two parallel systems incorporating CT scanners according to an embodiment of the present invention.

Figure 3A:
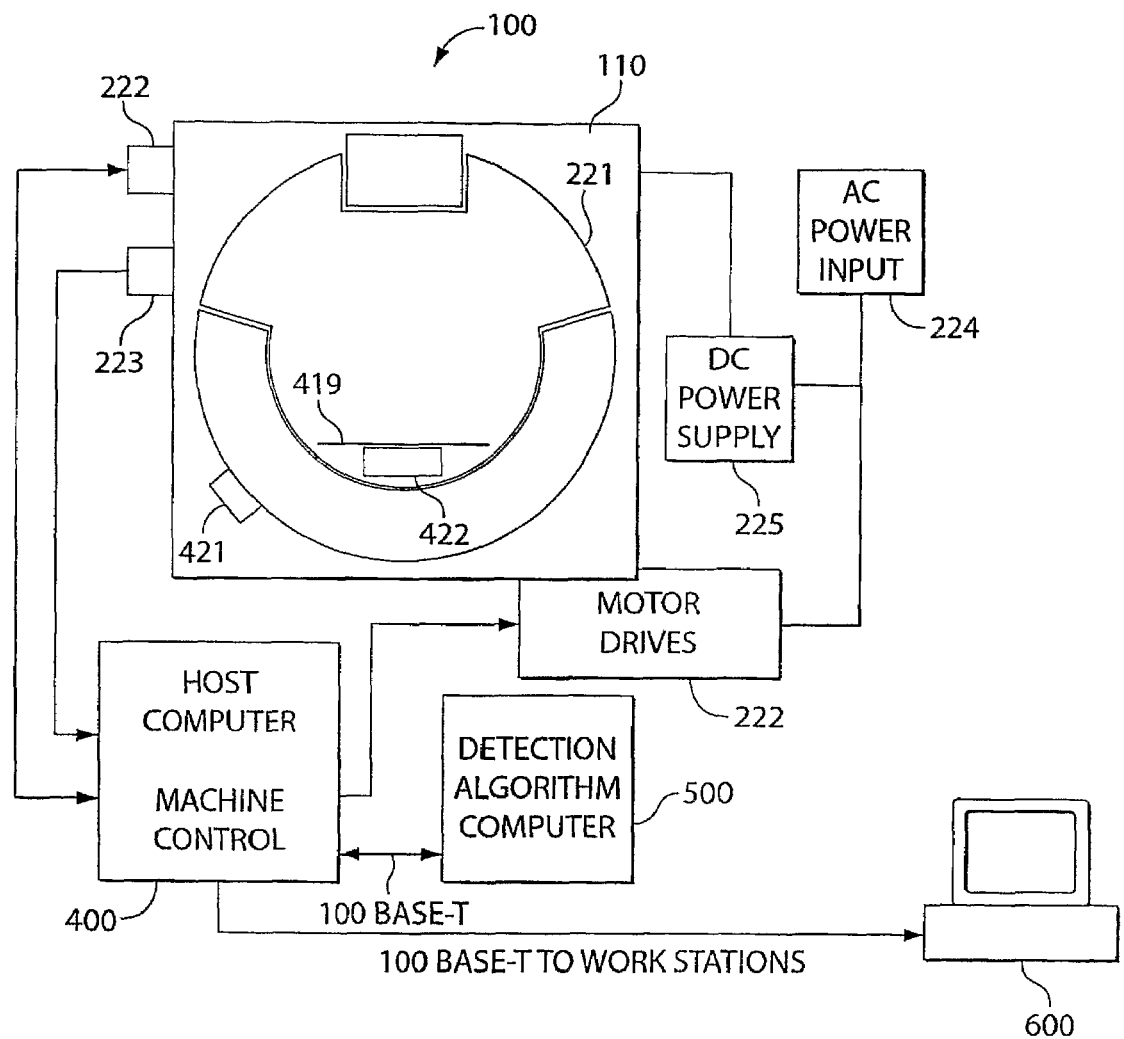
FIG. 3A is a block diagram of the components of a CT scanner system incorporating a CT scanner, such as the CT scanner shown in FIG. 1, according to an embodiment of the present invention.

FIG. 3A illustrates the components of a CT scanner 100 according to an embodiment of the present invention. The CT scanner 100 includes the gantry 221, and two computers 400, 500. A host computer 400 controls operation of the scanner and retrieves data from the detectors. A detection algorithm computer 500 operates on the data to determine whether an explosive device or other object of interest is present. Of course, a single computer could be used to perform all of the functions for the CT scanner. However, the use of two computers prevents the extensive processing of the detection algorithm from slowing down the operation and data collection of the CT scanner. Also, control and data interfaces 222, 223 are connected between the gantry 221 and the computers 400, 500. An AC power input 224, connected to ordinary 240 V AC power, provides power for the CT scanner. A DC power supply 225 receives the AC power and converts it to DC power for powering the gantry electronics. A set of motor drives 222, powered by the AC power, or alternatively by the DC power, operates the conveyor and rotates the gantry. A data link 223 connects the detector assemblies to the host computer 400. DC power and the data link are positioned on the ring of the gantry to provide data during rotation. In one embodiment, the circuit boards 920 on the detector assemblies 900 (shown in FIG. 3C) collectively sample the detectors 1440 times per second. The data is then transferred, through the data link 223 to the host computer 400. Encoders 421, 422 are used to determine the rotational position of the gantry and the linear position of the conveyor 419. This data is also provided to the host computer.

Figure 3B:
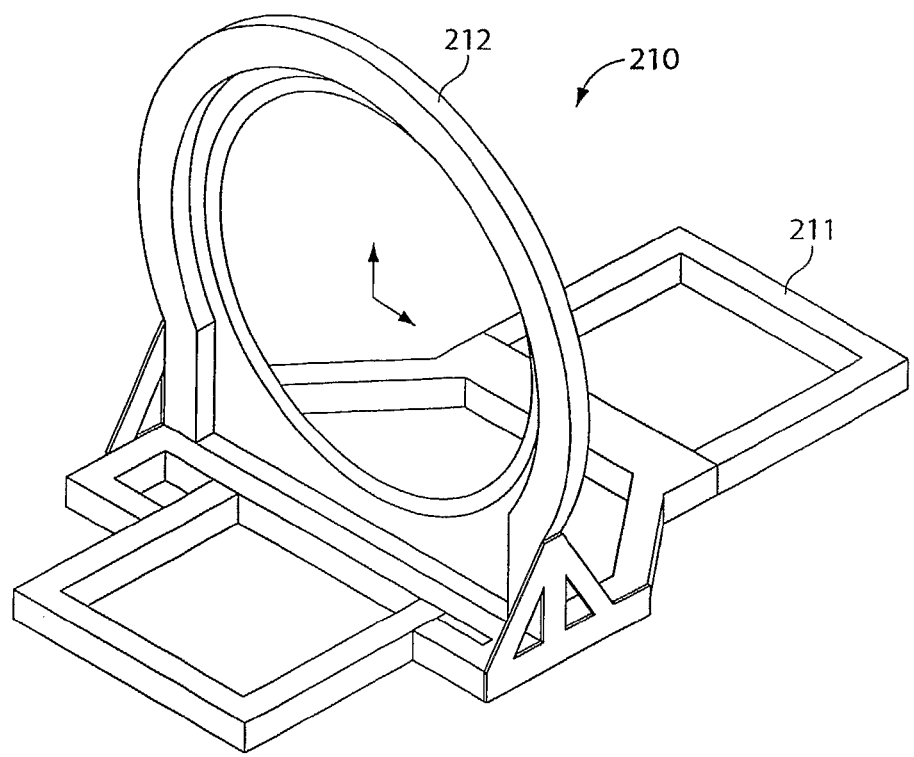
FIG. 3B is a perspective view of a gantry support structure for use with the embodiment of FIG. 3A.

FIG. 3B illustrates one embodiment of a gantry support system disposed within the x-ray area of the housing 110 (shown in FIG. 3A). The gantry system includes a support structure 210 (FIG. 3B) and a gantry 221 (FIG. 3A). The support structure 210 includes a base 211 and a circular shaped vertical support 212. The vertical support 212 is attached to the base 211. Conventional CT scanners include a computer on the gantry to process data from the detectors and format the data for transmission from the gantry to a host computer that operates the scanner. According to an embodiment of the present invention, the CT scanner does not include a computer on the gantry. Instead, data from the detectors is streamed directly to the host computer. Elimination of the computer on the gantry permits a smaller and lighter gantry. As with conventional CT scanners, the gantry includes an edge contact (not shown) for transferring power and control signals to the gantry and data from the gantry while the gantry is rotating. Of course, the present invention may include a computer on the gantry to perform some of the processing of data as in conventional CT scanners.

Figure 3C:
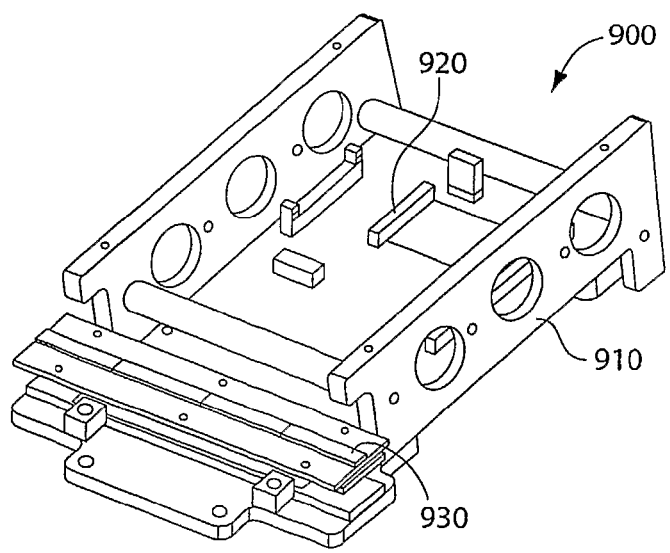
FIG. 3C is a perspective view of a detector array component of a CT scanner for use with the embodiment of FIG. 3A.
Figure 3D:
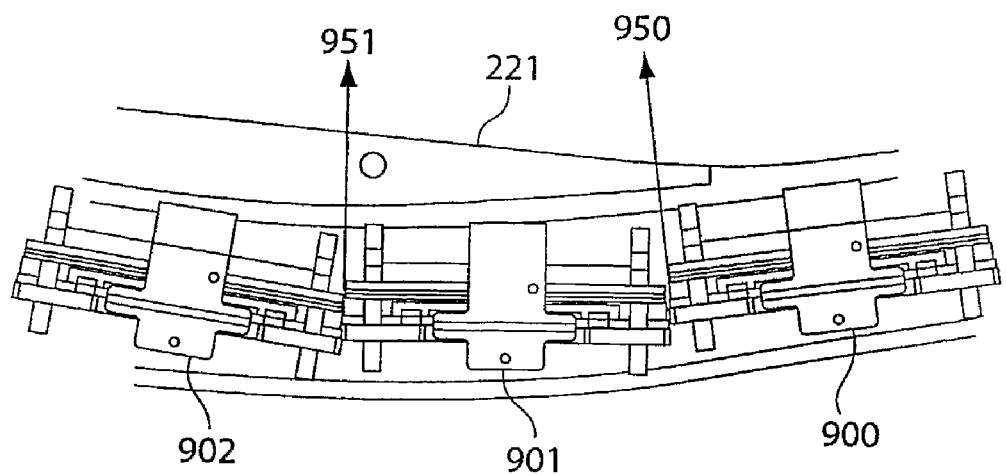
FIG. 3D is a front view of a portion of a detector of a CT scanner for use with the embodiment of FIG. 3A.

FIGS. 3C and 3D illustrate detector assemblies for simplifying the assembly of the CT scanner of the present invention and to improve quality control. FIG. 3C illustrates a detector assembly 900 having a housing 910, a processing board 920 and a detector array 930. The detector array 930 includes a plurality of detectors (not shown) arranged along the width of the assembly 900. As illustrated in FIG. 3D, detector assemblies 900, 901, 902 are attached to the ring of the gantry 221 (element 11 in FIG. 1). The detector assemblies 900, 901, 902 are positioned so that the detector at each end of the detector array 930 is adjacent to a detector on the end of an adjacent detector array. Ideally, for purposes of reconstruction, every detector in the array would be perpendicular to and equidistant from the x-ray source. However, with flat detector assemblies 900 there are slight variations in incidence angle and distance across the assembly. According to an embodiment of the invention, a detector assembly at the center of the detectors is arranged with a center detector element being perpendicular to the position of the x-ray source. For the remaining detector assemblies, the outermost detector element is perpendicular to the x-ray source. As illustrated in FIG. 3D, the x-ray source direction 950, 951 is perpendicular to the left hand side of an assembly on the left hand side of the gantry. The right hand side of assemblies on the other side of the gantry would be positioned perpendicular to the direction of the x-ray source. Such positioning allows the detector arrays to be properly angled and nested, as illustrated in FIG. 3D, to minimize the distance between adjacent elements on different assemblies.

Figure 3E:
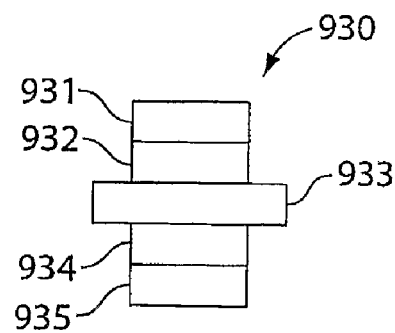
FIG. 3E is a cross sectional view of a detector component of a dual energy CT scanner for use with the embodiment of FIG. 3A.

According to an embodiment of the present invention, the CT scanner operates in a dual energy mode. FIG. 3E is a cross sectional view of one embodiment of a detector element 930 for dual energy operation. The detector element includes a low energy scintillator layer 931, a low energy photodiode layer 932, a copper layer 933, a high-energy scintillator layer 934, and a high-energy photodiode layer 935. The high-energy layers 934, 935 are wider than the low energy layers 931, 932. According to an embodiment of the invention, the low energy layers are approximately 5 mm long and the high-energy layers are approximately 10 mm long. The different lengths create similar flux levels between the low and high-energy layers, even with the greater shielding from the copper and additional layers, thereby simplifying data acquisition electronics and subsequent signal processing. More specifically, the pitch of the low energy detector and the pitch of the high energy detector are the same (in one embodiment, the depth of the low and high energy detectors are not the same; the low energy scintillator is significantly thinner then the high energy one). Alternatively, a dual energy scan can be performed using known techniques with a pulsing x-ray source and a single photodiode layer in the detectors. In yet another embodiment, layers 931, 932 are adapted to detect high and low energy x-rays and subtraction of the high-energy signal from layers 934, 935 produces a desired low energy signal. In one embodiment the average low energy is around 50 kV and the average high energy is around 100 kV.

Figure 4:
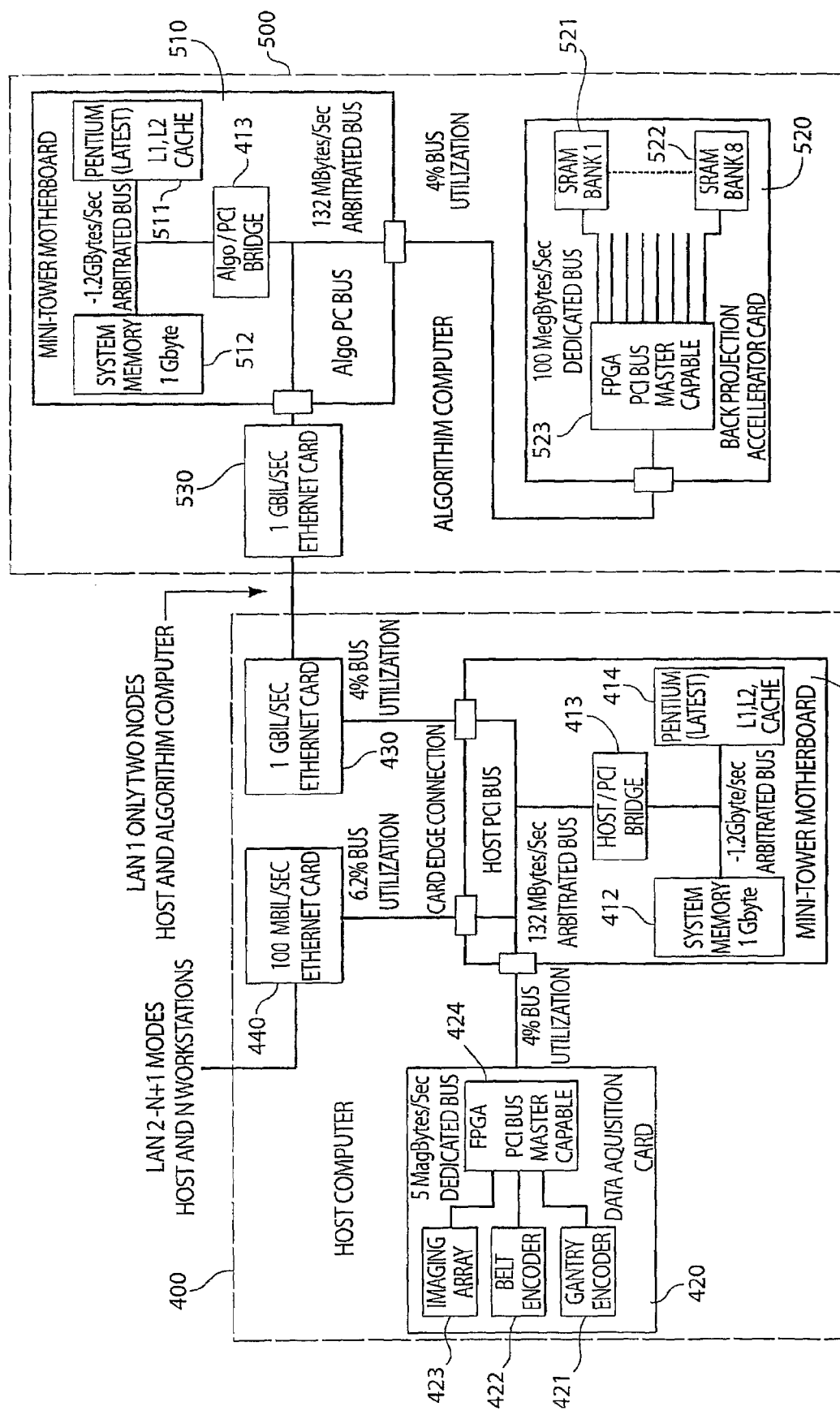
FIG. 4 is a block diagram of computer components of the CT scanner system of FIG. 3A.

The components of the computers are illustrated in FIG. 4. The host computer 400 includes a motherboard 410 and a data acquisition card 420. The data acquisition card 420 includes inputs from an imaging array 423, the conveyor belt encoder 422, and the gantry encoder 421. The imaging array is the collection of detector assemblies including detector assemblies 900, 901, 902 (shown in FIG. 3D) sending their data through data link 223. It also includes a field programmable gate array (FPGA) card 424 for retrieving the data and forwarding it to the motherboard 410. The FPGA card is a conventional FPGA card such as Model # ADM-XRC/405E-6, available from Alpha-Data of Stockholm, England. The motherboard 410 includes a processor 414, such as a Pentium® processor from Intel® Corporation of Santa Clara, Calif., and a large RAM 412. It also includes a standard Intel Host/PCI bridge for sending and receiving information from the data acquisition card and other computers. The data retrieved from the CT scanner is transferred to a conventional off-the-shelf detection algorithm computer 500 An Ethernet connection allows quick transfer of the large amounts of data. The detection algorithm computer includes a motherboard 510 for proper processing of the data and, in one embodiment, a back-projection accelerator card 520 for processing the data to determine the existence of explosives or other materials. The motherboard 510 includes a processor 511 such as a Pentium processor from Intel Corporation of Santa Clara, Calif., and a large RAM 512. It also includes a standard Intel PCI bridge for sending and receiving information from the data acquisition card and other computers. Reconstruction is performed on the same processor (i.e., CPU) 511 that runs the detection algorithm. In an embodiment that includes a back projection accelerator card 520, the card can include an FPGA card 523 coupled to a plurality of SRAM banks 521, 522. According to an embodiment of the invention, the detection algorithm computer 500 is programmed to process the data from the CT scanner in a manner, which allows a determination of the nature of contents of interest without a complete reconstruction of the entire contents. This method allows baggage to be scanned and processed at a faster rate than with conventional CT processing. The bag is scanned while it is moving on the conveyor belt and the gantry is rotating. In one embodiment, the data is analyzed in such a way as to take advantage of the fact that there are projection images at every angle. In one embodiment, the method allows for the automated finding in three dimensions of all the objects in the bag and the clutter around them. It is done at such a speed (5-10 cm of belt motion for every revolution) as to render the data unreadable as traditional projection data, and too sparse to be used for helical scanning. The advantages are that this mode of data acquisition allows the belt to move at a practical speed, e.g., at a constant speed (like a helical scanner) but requires significantly fewer detectors and less computer processing power.

In one embodiment of a method of the present invention, the data is analyzed from all 360 degrees and a suitable angle (per object in the bag) is selected to analyze the properties of the particular object. A better estimate (than Single Projection) for mass is achieved because the x, y and z position of the object in the bag are known. The length can be deduced by conventional edge following techniques and the high/low energy image ratio (if dual energy is used) could be used to determine the atomic number without a lot of expensive and complex basis space and background subtraction algorithms.

As noted above, in one embodiment, to collect dual energy data, the system incorporates dual energy "stacked" detectors, allowing measurement of both density and effective atomic number for each CT scan. Stacked detectors form an array that can measure both high and low x-ray energy. As noted above, in one embodiment the stacked array has a front row of detectors and a back row of detectors.

In one embodiment, the x-ray source maintains a constant flux, avoiding the need to switch energies during the scan. Since there are two types of detectors the dual energy information is available every time the system collects data.

The data acquisition system utilizes a 16-bit A/D converter with variable gains, such as XDAS-30 from Electron Tubes of Ruislip, England, to allow for the simultaneous readout of the signals from the front row detectors and the back row detectors. To calibrate the system one measures dark current (noise level without X-rays applied) and the "air" value (signal strength with the X-rays on and nothing in the beam). These measurements are used to calibrate and compensate for variations such as variations in X-ray output and detector sensitivity and variations of the materials in the "beam path." In other words, operators of a system according to the invention use conventional calibration techniques.

The present invention further provides a system for processing data from a CT scanner to check for contraband without complete reconstruction of the bag contents. Such a system is disclosed in U.S. Provisional Patent Application Ser. No. 60/442,246, entitled "Method and Apparatus for CT Scanning of Baggage," filed Jan. 23, 2003, and U.S. Patent Application entitled System and Method for CT Baggage Inspection, filed Jan. 23, 2004, both of which are incorporated herein by reference in their entirety.

Figure 5:
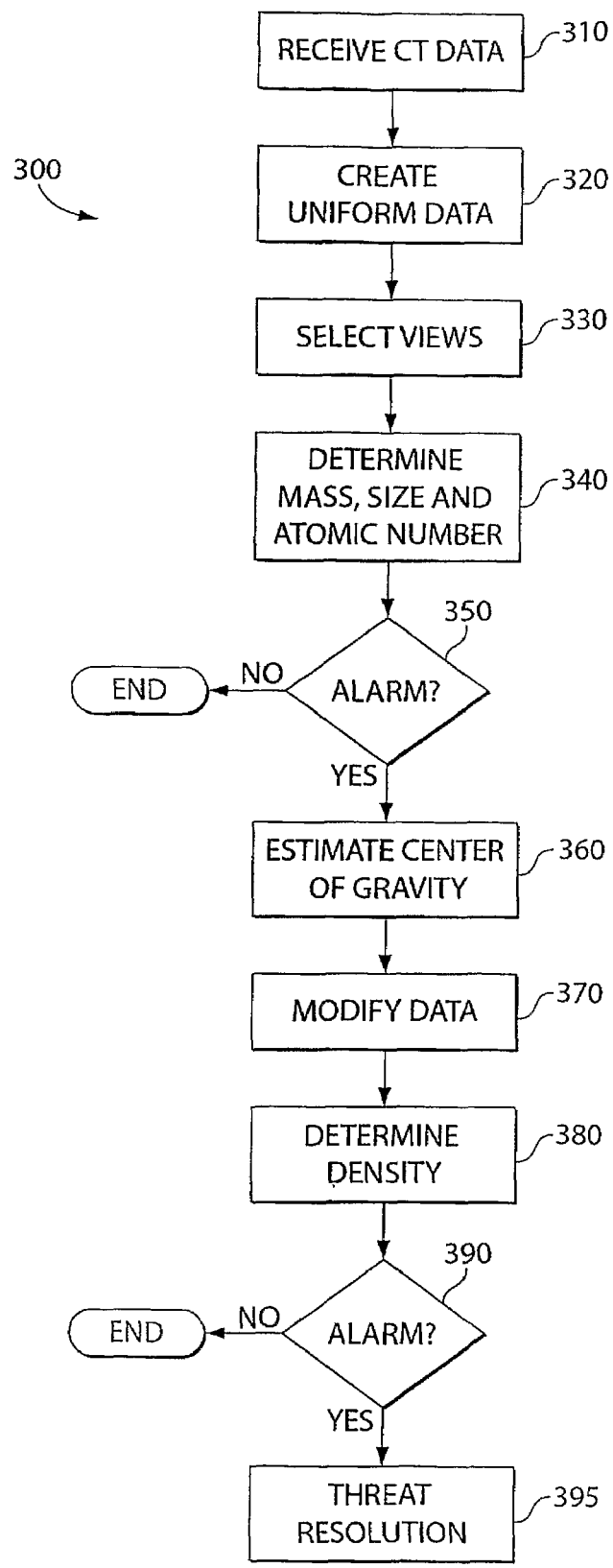
FIG. 5 is a block flow diagram of a CT data analysis process according to an embodiment of the present invention.
Figure 6A:
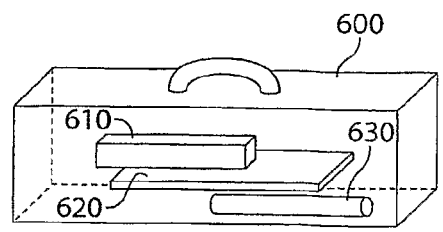
FIGS. 6A-6D illustrate a detection process according to an embodiment of the present invention.
Figure 6B:
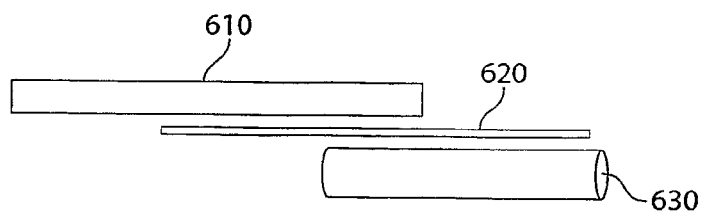

FIG. 5 is a block flow diagram of a process 300 for analyzing the CT scanner data according to an embodiment of the present invention. FIGS. 6A-6D illustrate the processing of the data according to an embodiment of the present invention. FIG. 6A represents a bag 600 to be scanned. Three objects of interest are shown in the bag, a Semtex block 610, a sheet explosive 620 and an aluminum rod 630. FIG. 6B illustrates a side view including detail of the objects as they correspond to the scanned data shown in FIG. 6C.

Figure 6C:
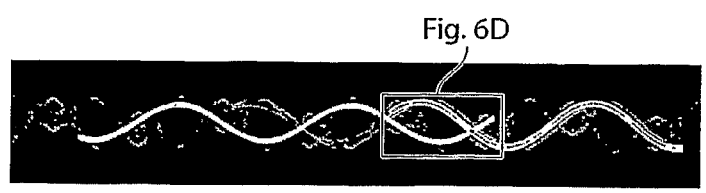

As a bag is scanned, the CT scanner generates a large quantity of data. The present invention operates with large quantities of data generated by a rapidly moving CT scanner. According to an embodiment of the invention, the gantry rotates at a specified rate, e.g., of 60 to 90 RPM, and the conveyor belt is moved at a specified rate, e.g., 5-10 cm/s. In this embodiment, the detector array is sampled at a constant rate, e.g., of 1440 lines per second. With reference to FIGS. 3A, 4, and 5, the detection algorithm computer 500 receives CT data, at step 310, from the CT scanner 221 and host computer 400. FIG. 6C is a lineogram representing the CT scanner data for objects in the bag. The lineogram represents the normalized (step 320) raw data obtained from the scanner. If the bag was stationary during the scan, then the lineogram could be referred to as a sinogram. Said another way, lineograms include standard sinograms (static CT scans) and moving sinograms (e.g., with a bag being scanned being moved through a CT scanner during a scan). Each vertical line of raw data represents the values at the detectors at a sample time. Since the x-ray source is substantially a point, each detector provides data from a different angle relative to the x-ray source. The raw data is processed so that each vertical position in the lineogram corresponds to a single plane in the bag (i.e., the plane being substantially perpendicular to the direction that the bag travels on the conveyor) and to a single angular projection of the CT scanner.

The normalization process (step 320) of a lineogram or a sinogram normally involves two steps. The two steps could occur in either order. Step 1 which is common to most x-ray systems, not only CT's, consists of the subtraction of dark data from both the object signal and the air signal. Usually, the dark subtracted signals are then linearized by taking the natural log. The two linearized, dark subtracted signals are then subtracted from each other (usually the object data is subtracted from the air data to obtain positive values) to obtain the air normalized data. Alternatively and mathematically equivalent, would be to take the ratio of the two dark subtracted signals and then take the natural log. Step 2 involves the parallelization of the data. This makes the data look like it was taken with a parallel beam x-ray instead of a fan beam x-ray. Other techniques may be used for reconstruction, e.g., using existing methods for reconstructing a CT image from fan beam data, but the described technique is desirable, because it simplifies the process of reconstruction and analysis.

The present invention uses known techniques for processing of CT scanner data to create the uniform lineogram data. One embodiment of the invention takes the natural log of the ratio of a dark subtracted air signal to a dark subtracted object signal. However, the data is not reconstructed to obtain three-dimensional voxels of the entire contents of the bag. Rather the uniform data is left as a lineogram. Furthermore, while FIG. 6C illustrates the lineogram data as it could be displayed on a monitor, the system does not necessarily display any such data. The data is merely processed in the detection algorithm computer 500. However, FIG. 6C, and other figures representing lineograms, are presented to indicate how the data is processed. This approach for acquiring CT data can be referred to as a Tomographic and Transmission Analysis Lineogram scan (ToTALScan).

Figure 6D:
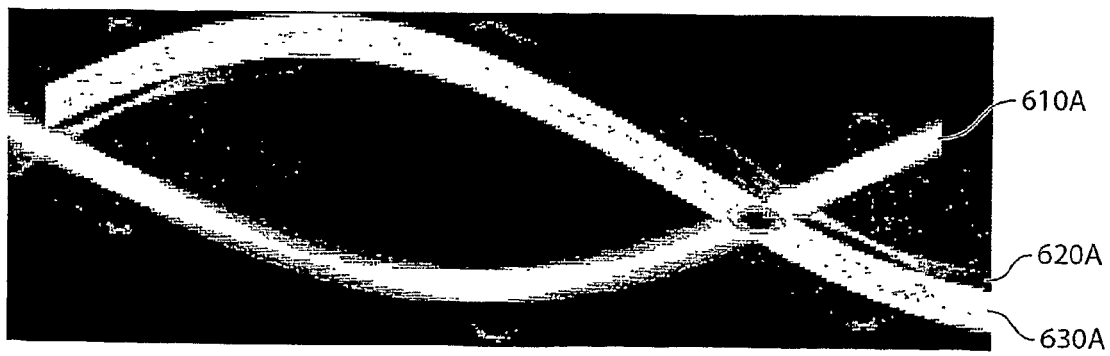

In FIG. 6C each object appears as a substantially sinusoidal line, i.e., a sinogram, in the lineogram. The horizontal dimension in the data, FIG. 6C, corresponds to the horizontal position within the bag. One can use the data in the vertical dimension to determine the position of the object from the x-ray source. The vertical dimension changes for the object as the angular position of the x-ray source changes during rotation. The detection algorithm computer 500, processes the data to analyze each object represented by a sinusoidal line. FIG. 6D illustrates a detail area of the image in FIG. 6C. The detail shows where the data from various objects overlap and areas where objects are separated.

According to the present invention, each object is analyzed separately to determine whether or not it might be a threat. For a proper analysis, the objects in the bag must be separated. At step 330, one or more views of an object are selected so that objects are separable from the clutter around them, i.e., other objects. The mass or attenuation of each object represented by a line is calculated during the scanning process.

Figure 7A:
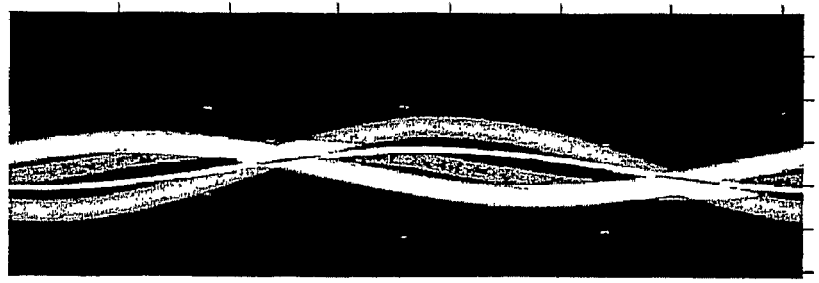
FIGS. 7A-7B illustrate determination of clutter from scanned data.
Figure 7B:
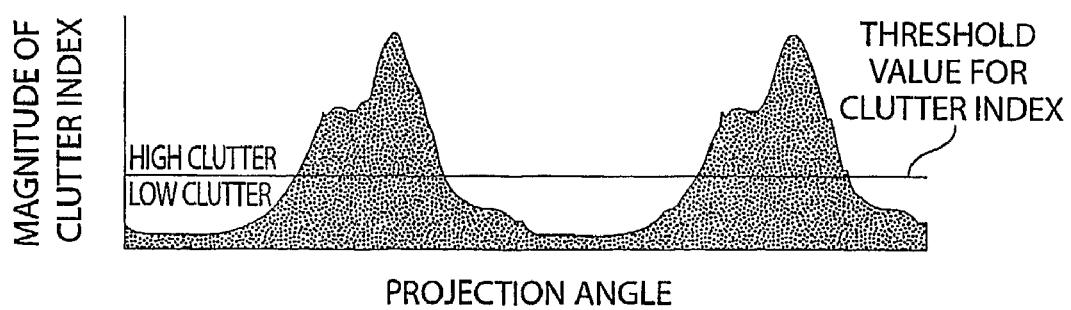

A clutter index is then calculated for each slice of the data. The slice in this context is not the same as a "slice" of reconstructed CT data. In conventional systems, the voxels for the entire bag are reconstructed. A voxel is a unit of graphic information that defines a point in three-dimensional space. Since all of the voxels are known, a "slice" can be represented from any angle, the slice including the voxels in the plane of the slice. Additionally, a single rotation of the gantry in a start/stop CT scanner is also called a slice. With respect to the present invention, the clutter index is based upon a vertical line through the lineogram and corresponds to a single plane in the bag (i.e., a plane that is substantially perpendicular to the direction of travel of the bag) and also a single projection angle. The clutter index represents how evenly the mass is distributed along the width of the bag for a given projection angle. A high clutter index represents areas where objects likely overlap. A low clutter index identifies projection angles where the objects are most likely separated and where their properties can be more accurately calculated. FIGS. 7A-7B illustrate a determination of object clutter, which can be used to select views for analysis of the CT data. FIG. 7A is a lineogram for a bag and FIG. 7B is the corresponding clutter index. In FIG. 7A, the x-axis represents the projection angle and the y-axis represents the magnitude of the clutter index. A threshold value is used to determine areas of high clutter and areas of low clutter.

Figure 8A:
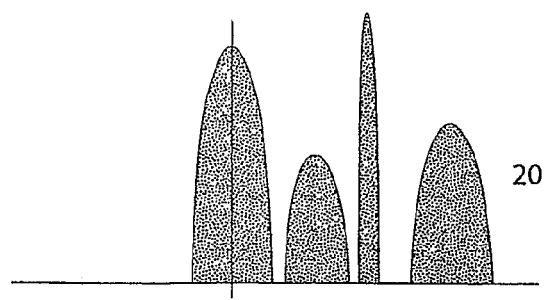
FIGS. 8A-8C illustrate object data from different angles in a low clutter area.
Figure 8B:
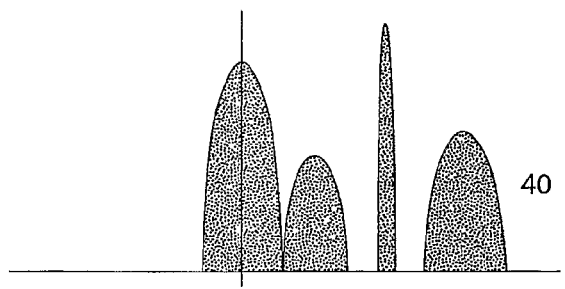
Figure 8C:
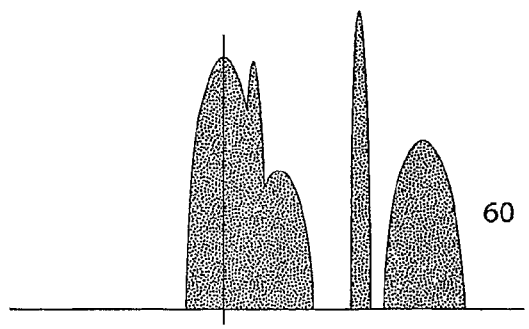
Figure 9:
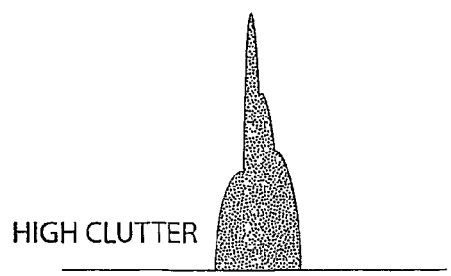
FIG. 9 illustrates object data in a high clutter area.

The data at the low clutter areas are analyzed to determine objects of interest. FIGS. 8A-8C illustrate data obtained when the x-ray source is at three different angles (i.e., 20, 40 and 60 degrees) relative to a home orientation (assigned 0 degrees), e.g., an orientation in which the x-ray source is located directly above the conveyor belt. The data in FIGS. 8A-8C correspond to low clutter areas. The x-axis represents detector number, and the y-axis represents raysum (mass). The data shows several distinct objects. FIG. 9 illustrates the same object data at a high clutter angle, in which the objects cannot be distinguished.

Returning to FIG. 5, at the low clutter views selected at step 330, the objects are analyzed, at step 340, to determine mass, size, metallic content, location, Z-eff, and atomic number for each object. In one embodiment two views are used to determine the mass of the object. An object located in one view is compared to objects in a second view to find a closest match. Additional views can be used to increase the reliability of the system. If an object cannot be reliably located in multiple views, then the bag should be noted for further review and possible hand search. The use of multiple views allows a determination of the x,y position of the object in the bag. The exact position allows calculation of the magnification of the object, its dimensions, and, hence, the mass per unit length of the object. The length of the object can be determined from the length of the lineogram corresponding to that object. The determined information is compared to preselected criteria to determine whether an object is a potential threat. Since objects are located and analyzed based upon slices of the bag, processing can occur simultaneously with the scanning process and does not have to wait until all data is collected.

If no potential threats are located in the initial analysis, the bag is cleared, at step 350 and continues onward in the baggage handling system. However, if any potential threats are identified, the analysis continues at step 360. Furthermore, the analysis commencing with step 360 does not have to await complete scanning of the bag. At any time during the processing, an object can be identified as a potential threat and subjected to further analysis. In this manner, the processing of a bag is expedited. The processing at step 360 seeks to locate and analyze a single object. An object which is perfectly positioned parallel to the axis of rotation of the gantry would create a true sine wave. However, objects generally have other orientations. The first step in the secondary analysis process is to determine and correct for the path of the object.

Figure 10A:
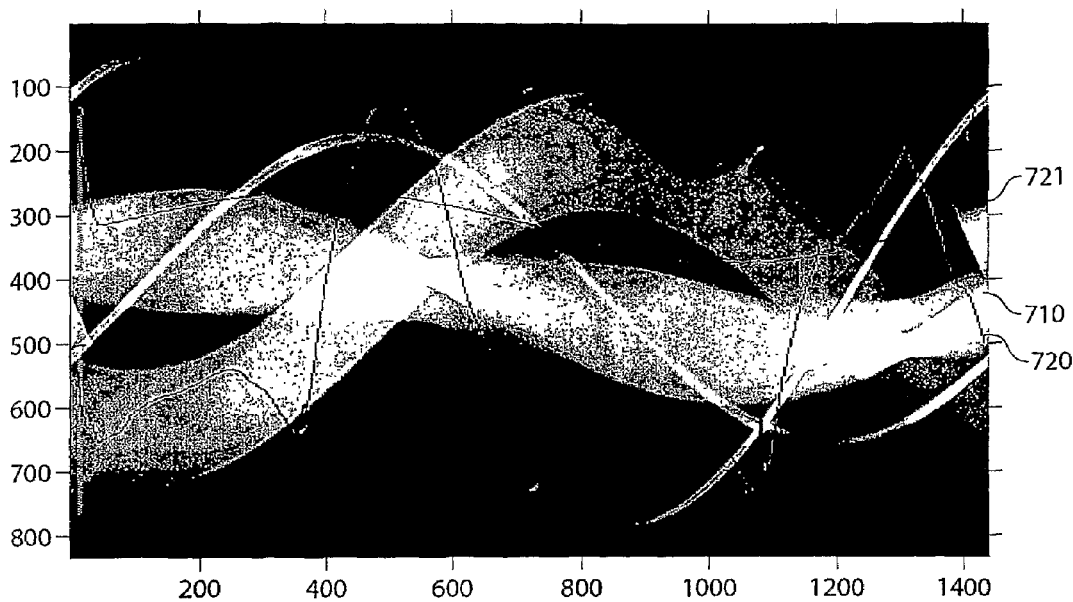
FIGS. 10A and 10B illustrate a data modification process according to an embodiment of the present invention.

At step 360, the center of mass of the object of interest is estimated. To locate the center of mass, two points along the lineogram associated with the object of interest are located. These points are located at areas of low clutter and at the center of mass of the object of interest along the particular slice. The center of mass of the correct object is more easily determined at the areas of low clutter because other objects are not contributing to the data at such locations. FIG. 10A is a lineogram having an object of interest 710. The mass clutter indices 720, 721 are superimposed on the lineogram to illustrate areas of low clutter. The center of mass line of the object of interest can be estimated based upon the two points representing low clutter.

Figure 10B:
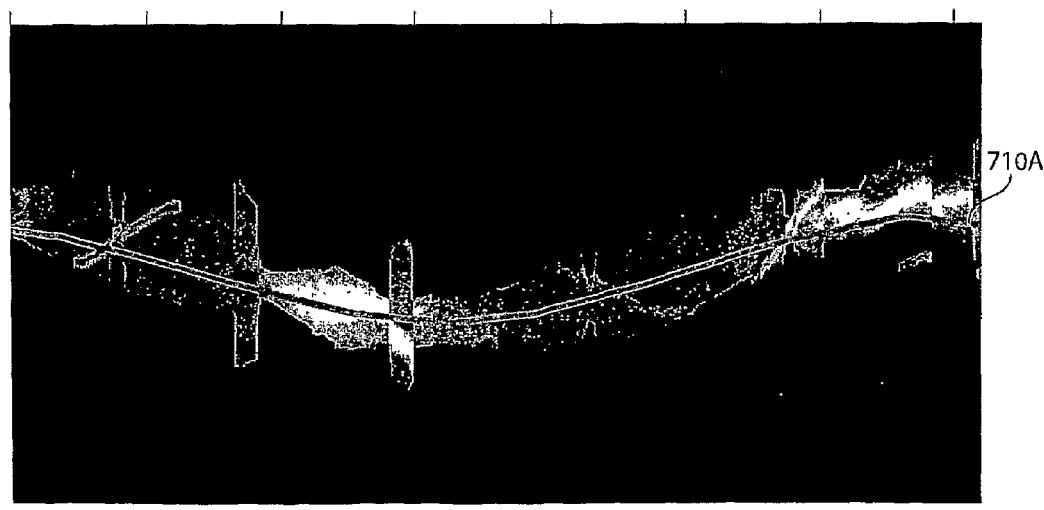

At step 370, the object data is modified so that the object projections are on a desired sine wave. The sine wave is selected to pass through one of the two selected points. It does not matter which point is selected as this only effects an x-y translation. The object data is modified by eliminating all other objects and moving the projections of the object of interest from the center of mass line to the selected sineogram. FIG. 10B illustrates the modified data for the object of interest 710 of FIG. 10A. The modified data is used to reconstruct the object of interest. All other data is ignored. Since only a small portion of the data is used in the reconstruction, the process can be accomplished quickly. Furthermore, the reconstruction is clearer since it is limited to the object of interest.

Figure 11A:
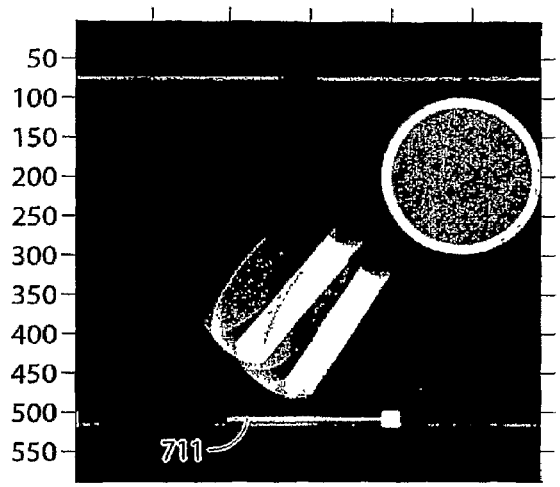
FIGS. 11A-11C illustrate reconstruction of data subjected to the modification process of the present invention.
Figure 11B:
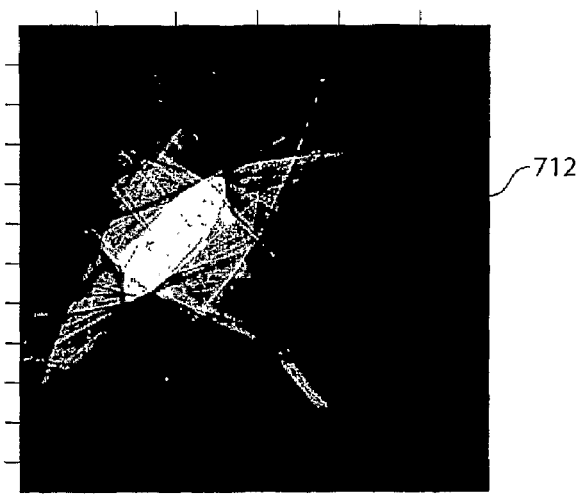
Figure 11C:
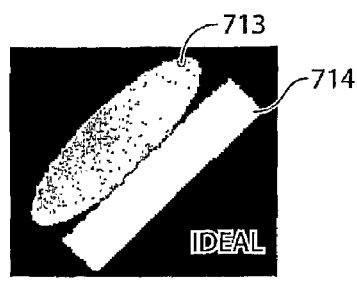

FIGS. 11A-11C illustrate the effect of data modification on reconstruction. FIG. 11A represents a reconstructed image using the original data. The object of interest 711 is unclear within the confusion of other objects. FIG. 11B illustrates the reconstruction from the modified data. The object of interest 712 is clearly focused and visible. FIG. 11C illustrates the actual contents of the bag in which an explosive material 713 is adjacent to a thick piece of metal 714.

From the reconstructed data, the density of the object can be determined step 380 by reconstructing the modified sinogram. Again, at step 390, a determination is made as to whether a potential threat exists. If no threat exists, the bag is cleared. Otherwise, other resolution mechanisms are used at step 395. Steps 360 and 370 and optionally steps 380 and 390 can be referred to as a "SnapScan" method.

Other resolution mechanisms may include review of a reconstructed image by an operator, additional scans of the object of interest, or hand search. If operator review is required, the relevant CT image is reconstructed from the scanned data in a conventional manner. Techniques/algorithms to perform conventional CT reconstruction from scanned data are available in Software packages (like Matlab available from The MathWorks, Inc. of Natick, Mass.) and in open source code such as that available from The Open Source Computed Tomography Simulator (Manual ctsim-manual-latest.pdf (last modified Sun, 2, November 2003); Source Code Unix (.tar.gz) ctsim-4.3.1.tar.gz (last modified Sun, 2, Nov. 2003) Windows (.zip) ctsim-4.3.1.zip (last modified Sun, 2, Nov. 2003); Binaries-Linux Binaries/Debian Linux ctsim-doc__3.5.8-1_all.deb (last modified Fri, 9, Aug. 2002), ctsim-help__3.5.8-1_all.deb (last modified Fri, 9, Aug. 2002), ctsim__3.5.8-1_i386.deb (last modified Fri, 9, Aug. 2002) RedHat Linux ctsim-3.0.3-1.i386.rpm (last modified Tue, 20, Feb. 2001); Windows Binaries ctsim-bin-3.5.5-pre-release.zip (last modified Thu, 20, Jun. 2002), ctsim-installer-win32-3.0.3.exe (last modified Thu, 22, Feb. 2001) [retrieved on Jan. 3, 2005] Retrieved from the download web page of The Open Source Computed Tomography Simulator web site using Internet <URL: http://ctsim.org/download.html>). Furthermore, techniques/algorithms to perform conventional CT reconstruction from scanned data are described in books such as 'Principles of Computerized Tomographic Imaging' by Avinash C. Kak and M. Slaney, IEEE Press 1998. The reconstructed data is presented in visual form to the operator, along with an indication of the area on concern. The operator may then clear or stop the bag.

Dynamic Threat Resolution

Figure 12:
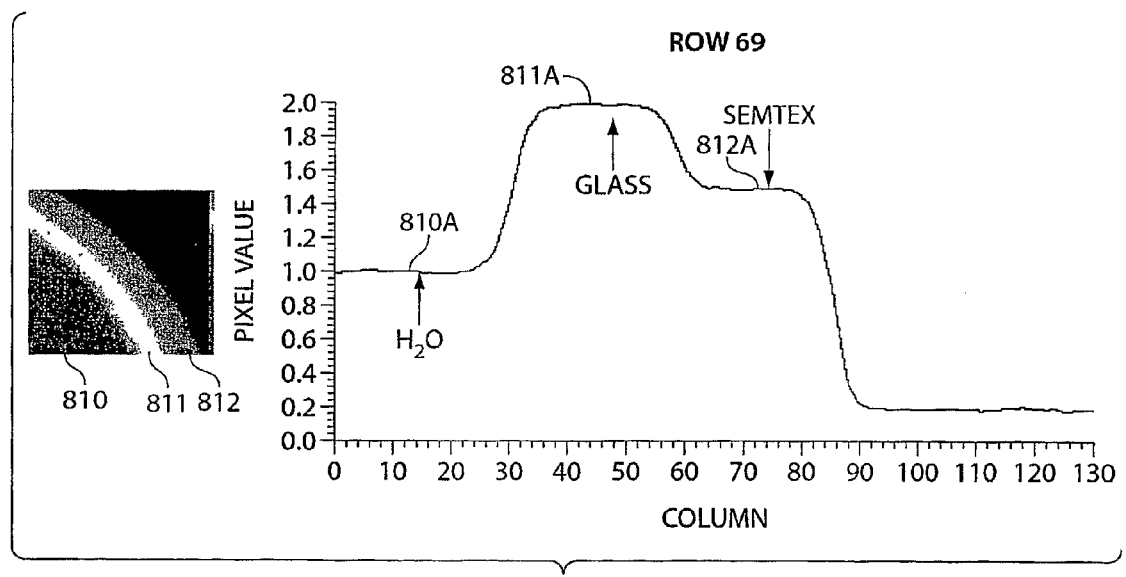
FIG. 12 illustrates reconstruction of data at an area of interest in a bag.

Alternatively, the bag can be returned to the CT scanner and a high resolution, dual energy scan performed. Since the location of the object of interest, in x, y, and z, is known from the previous processing, the entire scan need not be reconstructed. FIG. 12 illustrates reconstruction of a 2 cm square of an object of interest. The dual energy scan and high resolution allows detection of an ultra-thin sheet of explosive around a glass bottle of water.

The analysis of the present invention aids in review of bags and can be performed rapidly. The system of the present invention can be used as a level 1 machine, running at roughly 300 to 360 bags per hour (10-12 seconds/bag), through a first alarm stage. A lineogram image is analyzed for explosives in 10-12 seconds. Of course, the throughput could be increased by running the belt faster and rotating the gantry faster. In such a situation, processor speed may need to be increased, or an additional processor added, where bags could be ping-ponged between the 2 processors. If the bag is cleared the bag is sent on its way, e.g., to an airplane. If not, the system can automatically take more dual energy higher resolution CT slices of the alarming objects (typically 1 or 2 per alarming bag in the airport context). It is estimated that the algorithm will be able to clear 50 to 75% of such alarms, with an additional 2-5 seconds of analysis. The remaining alarms are sent to a workstation, where an operator looks at the images and decides whether to clear or otherwise rescan the bag, open it or 'sniff' it.

According to another embodiment of the invention conventional ¼ detector shift techniques, such as those contained in "Principles of Computerized Tomographic Imaging" described above<can be used to reconstruct higher resolution CT images for the slices where the lineogram analysis alarmed. The CT capability can be treated as a level 2 mode for alarm resolution\

Since analysis of a bag proceeds simultaneously with scanning, an alarm can be addressed while the bag is still in the scanner. If analysis of the data indicates a potential threat that cannot be resolved through data modification and reconstruction, the bag can be immediately subjected to a high-resolution scan. This can be done by slowing down the gantry or the conveyor belt. A high-resolution image can be created and presented to an operator for review. If the gantry is slowed to about 10 RPM and the bag moves at a high speed of about 1.5 m/sec, a high-resolution line projection image can be obtained and presented to the operator with an overlay of the threat position. Alternatively, if the conveyor belt is slowed to about 1 cm/sec, a full 3D image of the bag using standard helical CT algorithms can be generated and presented to the operator. As set forth in the description above, CT data are acquired using ToTALScan. The dual energy data is collected by sampling the detector array at a constant rate, e.g., at 1440 lines per second, with the gantry rotating a specified speed (e.g., 60 or 90 RPM) and the bag moving through the system at a constant substantially uniform speed (e.g., 5 or 10 cm/s). A line is one sample of an entire array of detectors. In one embodiment this sample is taken 1440 times per second, which, at 60 RPM, is 1440 times per rotation. One can also refer to the number of "lines" taken per rotation as the number of "views" taken per rotation. This technique allows collection of extremely high-resolution data of the entire bag for analysis. In one embodiment, with a ¼ detector shift alignment, the system first scans with a resolution of 1.6 mm/pixel. If the system finds anything of interest, the system can perform an analog zoom for the target and achieve resolution of 0.5 mm/pixel. The technique makes use of the massive amount of raw data available via ToTALScan (e.g., up to 288 lines per cm) in its native format rather than performing all detection analysis using the less detailed condensed image after CT reconstruction.

Figure 13:
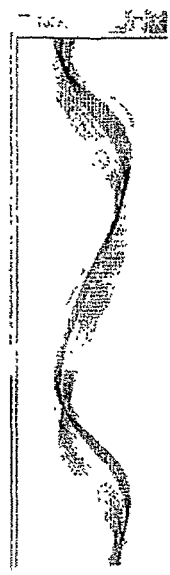
FIG. 13 is an image similar to FIG. 6C representing data for contraband detection analysis according to the embodiment of the present invention shown in FIG. 3A.

FIG. 13, similar to FIG. 6C, illustrates sinusoidal data from a CT scanner used in the ToTALScan technique. As noted above, each sinusoidal line in FIG. 13 represents an object in the baggage. A system according to one embodiment of the invention using this technique differentiates objects by mass, density and atomic number. The objects are then analyzed to eliminate objects that lack characteristics of possible contraband. Explosive compounds such as nitroglycerin (NG), pentaerythritol tetranitrate (PETN), hexahydro-1,3,5-trinitro-1,3,5-triazine (RDX), and octahydro-1,3,5,7-tetranitro-1,3,5,7-tetrazocine (HMX) are well known. For PETN, the constituent molecules each contain 8 Hydrogen, 5 Carbon, 4 Nitrogen and 12 Oxygen atoms. This makes the effective atomic number theoretically calculable (7.43) and the density is around 1.5 gr/cc. While analyzing the contents of a bag, if an object of sufficient mass is found that has an effective atomic number of about 7.4 and a density of about 1.5 gr/cc, the system alarms.

Figure 17:
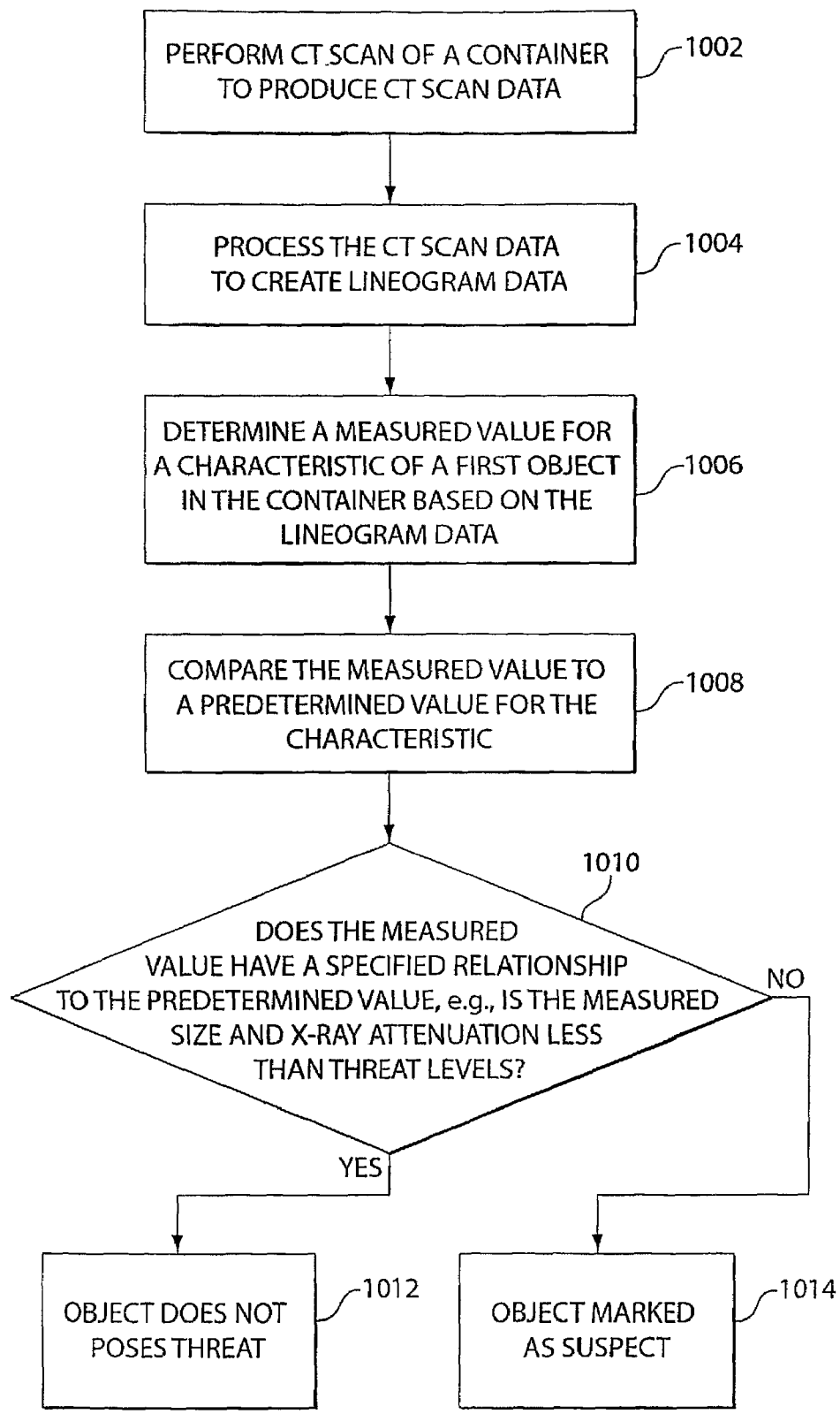
FIG. 17 is a flow chart illustrating a method for scanning a container to determine if the container poses a threat using, for example, the embodiment shown in FIG. 3A.

Thus, with reference to FIG. 17, one embodiment of the invention provides a method for scanning a container to determine if the container poses a threat. The method includes: performing 1002 a rotating scan of the container to produce rotating scan data; processing 1004 the rotating scan data to create lineogram data; determining 1006 a measured value for a characteristic of a first object in the container based on the lineogram data; comparing 1008 the measured value to a predetermined value; and if the measured value has a specified relationship 1010 to the predetermined value then determining 1012 that the object does not pose a threat. Alternatively, if the object does not have the specified relationship, the system can mark 1014 the object as suspect for further processing.

In one embodiment, the method further includes reconstructing lineogram data into a "ToTAL Slice" and analyzing the ToTAL Slice for absence of contraband.

Figure 14:
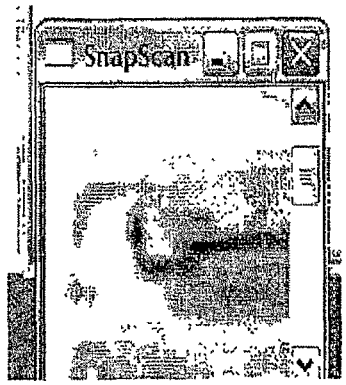
FIG. 14 is an image representing a partial reconstructed image according to the embodiment of the present invention shown in FIG. 3A.

The system can further acquire a "SnapScan" image, illustrated in FIG. 14, of object(s) that the system has not eliminated. One embodiment of a SnapScan method was described above with reference to FIG. 5. As noted above, Snapscan is a CT image reconstructed from the TotalScan data. SnapScan corrects for motion distortion by "focusing" in on objects of interest (i.e., objects that were not previously eliminated) and reconstructing only small portions of the entire bag. The system can calculate SnapScan in real time while the bag is moving through the gantry. In one embodiment, SnapScan provides density, mass, and atomic number information without having to stop the bag and acquire a full CT slice.

The system can use SnapScan to reduce the amount of reconstruction or review required. Potential threats can be reconstructed using the SnapScan technique, without the need to reconstruct the contents of an entire bag. The reconstructed object may be further analyzed by the system to determine whether it constitutes a threat. One embodiment of a system according to the invention eliminates objects lacking necessary size, density or shape as a threat, e.g., a weapon, without operator review. An operator need only review images for potential threats, e.g., weapons. The system may provide images of only the objects of interest, or may highlight portions of a bag that are of interest. Thus, the operator is not overloaded by non-threatening objects within a bag and can concentrate on the potential threats.

Figure 15:
FIG. 15 is a reconstructed image of a bag according to the embodiment of the present invention shown in FIG. 3A.

Furthermore, the data can be analyzed to create high-resolution CT slices as with conventional CT scanners. FIG. 15 illustrates such an image. Objects may be located within the CT slices or reconstructed as three-dimensional objects for review by the system or an operator. The size (number of pixels) to be reconstructed is arbitrary. One can always chose to reconstruct with more pixels. Going from 512 by 512 to 1024 by 1024 image however requires 4 times the reconstruction computer time. Thus, in one embodiment, a system using SnapScan can reconstruct a smaller portion of the image with an arbitrary number of pixels, to minimize the computer reconstruction time and maximize the resolution. For example, if a system processes only the lower quadrant of a 512 image and reconstructs it with 512 pixels, the system can double the resolution without incurring any extra reconstruction time. However, a system cannot keep zooming in, beyond the actual resolution of the image and continue to improve the resolution.

Threat Exclusion

One embodiment of a system according to the invention also has the capability of acquiring a high-resolution dual energy x-ray projection images of an object by stopping (parking) the gantry and moving the object rapidly through the x-ray beam.

A system according to one embodiment of the invention can automatically eliminate as a potential threat many types of objects that pass through a checkpoint. Objects such as coats, clothing, shoes, coins, and change trays, lack characteristics of a threat. In one embodiment, the system can determine that these objects lack characteristics of a threat based on x-ray attenuation and size data obtained via projection x-ray data. This information can be incorporated into an automatic decision process through an x-ray pre-screener attached to a small footprint CT scanner or by parking the gantry (i.e., stopping the gantry from rotating and obtaining a projection x-ray). In one embodiment, the system can eliminate further items as a weapon by adding in the density and "Z" information, available from the TotalScan data. TotalScan analyzes an object and determines if there is sufficient mass (and/or other characteristics) to be a threat, such as an explosive or weapon, including any weapons on the TSA prohibited items list. If an object lacks sufficient mass, density or other characteristic, no further review or analysis is required, including reconstruction of an image or presentation of the image to an operator for review.

If an object is determined to have not enough mass, x-ray attenuation, and/or size to be a possible threat (e.g., a weapon) reconstruction of the bag is not required. It can be passed without farther analysis or operator review. It is possible that one embodiment of such a system could automatically clear up to 40% or more of the objects inspected at a checkpoint in this maimer. Eliminating the need to review images provides labor savings and throughput increases at the checkpoint.

The present invention provides an innovative process in that a conventional Explosive Detection Scanner and specifically conventional CT scanners, dual energy and/or multi-view x-ray scanners use sophisticated algorithms to compare objects to threat material scanned in the lab. If there is a sufficient match to a large number, e.g., hundreds, of characteristics of a threat, the conventional systems automatically alert the user. The object and/or the alarm images are typically sent to an operator for resolution. An embodiment of the present invention approaches "detection" of weapons from the opposite perspective. An embodiment of the invention uses projection x-ray and/or CT technology to eliminate bags or objects as opposed to detecting them.

One embodiment eliminates objects based not on hundreds of characteristics but on only one or two characteristics (x-ray attenuation and size for example). These characteristics work uniquely well on carry-on objects as opposed to checked baggage because most (if not all) checked baggage would be too heavy or complex to be eliminated. Because of new security regulations, passengers are carrying more baggage and therefore placing more objects in an x-ray scanner than they used to do. This embodiment eliminates many of these objects (i.e. shoes, belts, coins, cell phones, coats, wallets) as potential threats.

Barrel Detection

Furthermore, one can fuse the above-described method of elimination with traditional detection methods. Once the system has eliminated certain objects, the system can accomplish detection of explosives using traditional methods of analyzing hundreds of characteristics using TotalScan data, and SnapScan and/or CT reconstructions. In one embodiment, the system can detect weapons, such as guns and knives, using similar techniques. These algorithms include but are not limited to another embodiment called "barrel detection".

Figure 18:
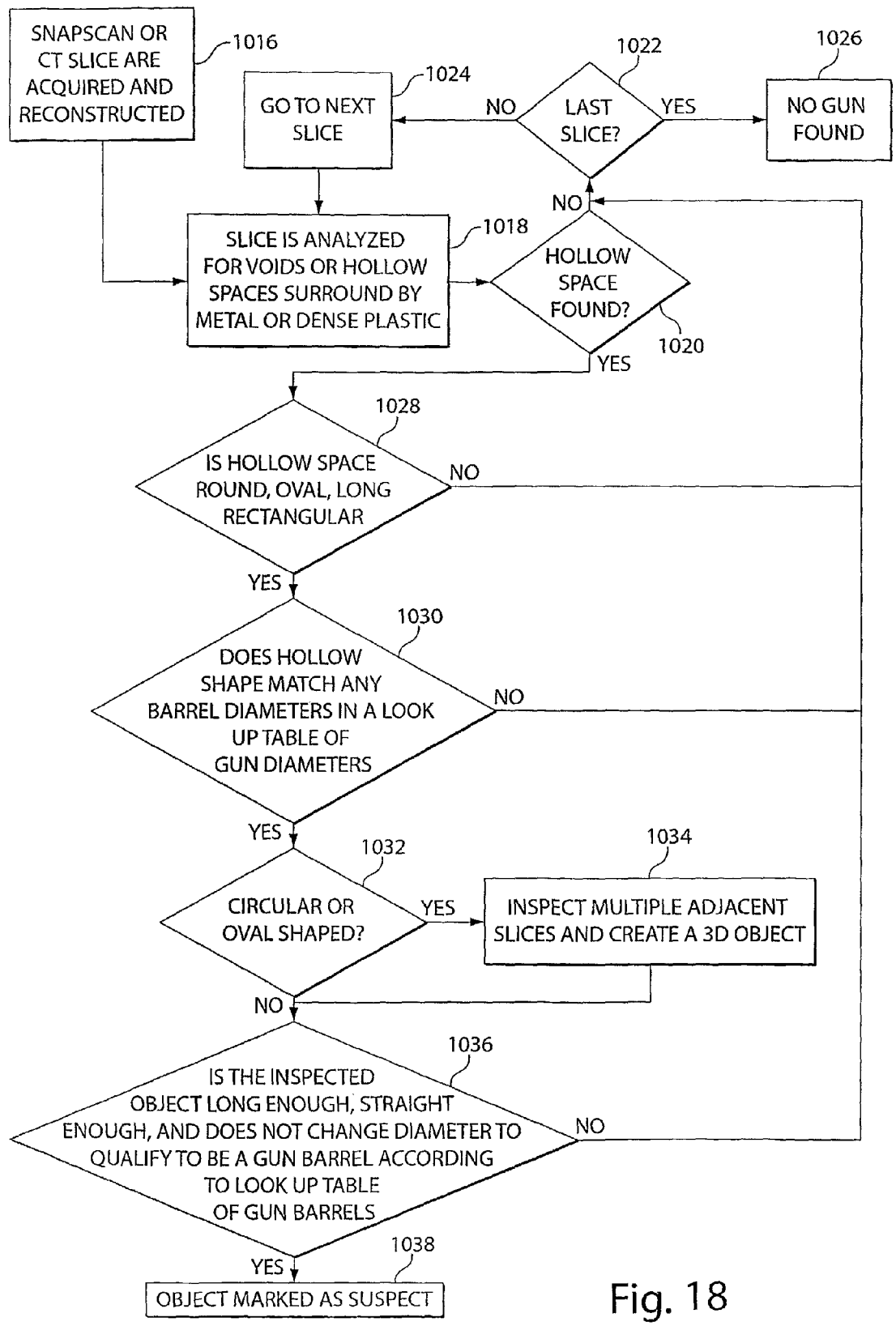
FIG. 18 is a flow chart of a barrel detection method according to one embodiment of the invention using, for example, the embodiment shown in FIG. 3A.

In one embodiment a system maintains a database of characteristics (e.g., the diameter) of a number (e.g., hundreds) of gun barrels and when the system detects a barrel shaped object, the system searches the database for a match. More specifically and with reference to FIG. 18, in one embodiment, a method according to the invention acquires and reconstructs 1016 a SnapScan or CT slice. The method analyzes 1018 the CT or SnapScan slice data to determine if a hollow circular or oval shape of a known diameter exists, the circular or oval shape being surrounded by metal or dense plastic. The method accomplishes this determination using conventional pattern recognition algorithms (including a measure for hollowness). If the barrel is placed relatively straight in a bag along the direction of the belt motion the hollow section will appear circular, if the barrel is at an angle the hollow area will appear as an oval. The closer the barrel gets to perpendicular to the belt motion the longer the oval hollow space will appear. If the barrel is exactly perpendicular to the belt motion the hollow barrel will run the length of the barrel and appear rectangular but only appear in one slice. In each of these cases the hollow section must follow an exact straight path. Since a gun barrel must be straight for effective use the hollow section will be measured in each successive slice (in the case of circular and oval configuration) to ensure the hollow section follows a straight line. The straightness will also be measured in the single slice perpendicular orientation.

Another measure is constant diameter over the length of the barrel. In other words, the hollow section must not change size over the length of the barrel. A gun barrel typically does not become wider or narrower over its length. By measuring these known parameters of gun barrels, all three of these configurations should be unique enough to distinguish barrels from other objects in bags.

Returning to FIG. 18, the method determines 1020 whether a hollow space is found. If not, the method determines 1022 if the method has analyzed the last slice for the container, e.g., bag, under inspection. If not, then the method goes 1024 to the next slice. If so, the method concludes that no gun was found 1026 in the container.

If a hollow space is found, the method determines 1028 if the hollow space is round, oval, or long rectangular. If so, the method determines 1030 whether the hollow shape matches any barrel diameters in a look up table of gun diameters. If so, the method determines 1032 whether the hollow is circular or oval shaped. If not, the method determines 1036 whether the object is long and straight enough and does not change diameter to qualify as a gun barrel according to a look up table of gun barrel characteristics. If so, the system inspects 1034 multiple adjacent slices and creates a 3D object and then performs step 1036. If the determination for steps 1028 or 1030 is negative, the method proceeds directly to step 1022. If at step 1036 the object does not qualify as a gun barrel, the method proceeds to step 1022 noted above. However, if the object does qualify as a gun barrel, the method marks 1038 the object as suspect for further processing.

Barrel detection is important because a gun can be taken apart and even separated into different bags to avoid detection. However, the barrel of a gun cannot easily be broken down. Images and data from a rotating x-ray technology, such as a CT scanner, are uniquely suited for barrel detection. CT scanners can detect the hole or void formed by a gun barrel. Techniques such as TotalScan, SnapScan, and CT reconstructions can be used to detect the void. In the total scan, a potential gun barrel appears as a very dense sinusoid. If the potential gun barrel has a hole, then the sinusoid has a distinguishable less attenuated center. In one embodiment, a system according to the invention uses other characteristics such as shape, mass, attenuation, and density in conjunction with barrel detection to detect weapons.

Figure 16:
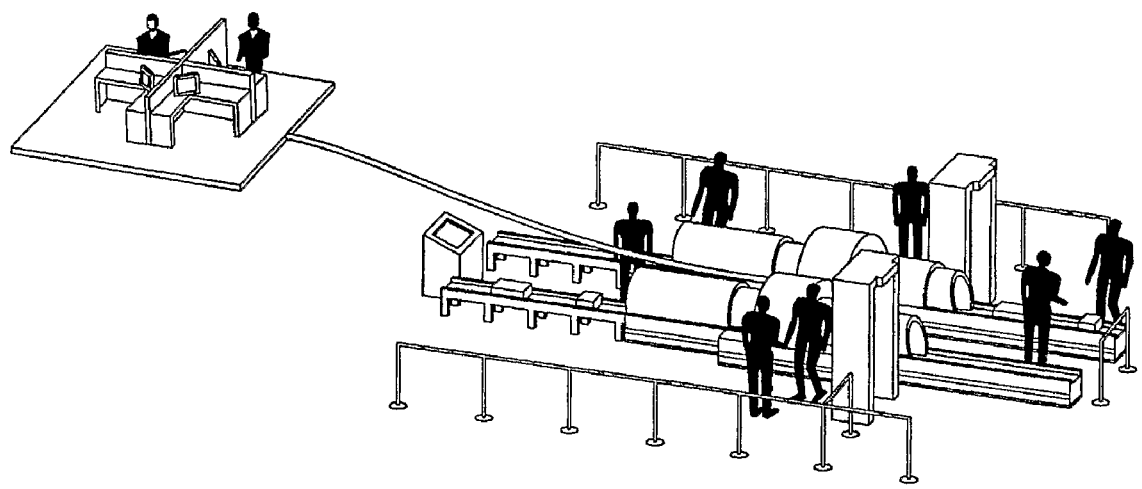
FIG. 16 is a view of a CT checkpoint scanning system according to the embodiment of the present invention shown in FIG. 3A.

Multiplexing Scanners:

Multiplexing scanners, i.e., connecting more than one scanner together into a network of scanners, reduces cost, space, and labor requirements. As illustrated in FIG. 16, small scale CT scanners can be placed close together, back-to-back in clusters of two, for example, at a checkpoint. The operator does not have to stand next to the machine. The multiplexed systems provide data from multiple scanners to a single control room. In one embodiment, a system includes both weapon elimination capability with multiplexed scanners. Today, screeners spend valuable time on, and their attention is strained by, inspecting objects that could not possibly be threats.

Threat Exclusion to Increase Throughput

In one embodiment, a CT scanner according to the invention can increase the velocity of its conveyor belt. If this embodiment eliminates all objects in a portion of a container/bag, the system accelerates the belt in the CT scanner to quickly move to the portion of the container/bag or to move to the next container/bag. In one embodiment, a system according to the invention can combine a CT scanner with an x-ray pre-scanner. In this embodiment, the system can eliminate bags/containers that cannot possibly contain a threat in the pre-scanner and rapidly ejects the eliminated bags/containers out of the CT engine, improving the overall operation of the system.

Hybrid Scanner Description

In another embodiment, the present invention provides a high throughput, high security checkpoint screening system. An adaptive system that inspects passenger baggage based on security intelligence inputs, such as CAPPS, can provide high throughput with improved security. Compared to today's carry-on inspection process, a carry-on EDS according to the present invention can improve security and double passenger throughput, with reduced screener labor. In other words, an embodiment of the present invention provides an inexpensive EDS system to double the throughput at the passenger checkpoint while improving the security screening process and lowering total screener labor costs.

Characteristics of this embodiment of the invention include:

Carry-on baggage inspection equal to, or superior to, today's carry-on inspection process for the majority of passengers.

Full EDS level screening for CAPPS selectee passengers eliminates the need for time consuming and labor intensive hand search of passenger bags.

Ability to leave laptop computers in their bags, thereby reducing the total number of objects to be screened (effectively increasing throughput)

Up to 600 bags per hour system throughput translates to over 7 passengers per minute (double today's carry-on inspection throughput)

Ability to "ratchet-up" the screening process whenever threat levels are increased Ability to perform full EDS screening for all passengers on elevated or high risk flights Fully multiplexed operation can save two to four screeners per checkpoint Ability to multiplex multiple checkpoints across an airport to further reduce labor while keeping checkpoint lanes open for passengers A single EDS system can replace two of the current carry-on inspection machines based on throughput For example, TSA, airports, airlines and passengers have lamented the need to inspect all passengers to the same level, regardless of their apparent or perceived threat to the aircraft. TSA has recently started screening CAPPS or CAPPS II selectee passengers differently than other passengers. This selectee screening process is time consuming, requires extra TSA labor, invasive to the passengers and very obvious to any who care to notice.

Deployment of EDS at checkpoints can improve the overall detection performance of the passenger screening process, and eliminate the need for redundant hand searching of selectee bags. Unfortunately, replacing existing carry-on inspection systems with EDS will be costly and could potentially slow the passenger screening process.

A new system is needed that improves overall security at the checkpoint without causing farther delays to the passenger screening process. An embodiment of the present invention improves the checkpoint throughput while increasing overall security standards.

According to one embodiment of the invention, a CT scanner incorporates an X-ray source and a detector array that are placed on a rotating disk (the "gantry"). The gantry spins at a specified speed, e.g., 60 RPM, during an automated EDS scan. If the disk is stopped, projection X-ray images similar to the images generated by today's checkpoint x-ray machines can be generated.

Different screening approaches may be used for standard and non-standard passengers. Non-standard, selectee passengers include CAPPS or CAPPS II selectees, passengers on high-risk flights, passengers that raise suspicion of a security agent such that the security agent deems a more thorough inspection to be appropriate, passengers randomly selected, e.g., to help improve overall checkpoint performance, etc.

According to one embodiment of a method according to the invention, all non-selectee passenger bags continue to be inspected using a standard projection image, similar to today's carry-on screening process. For a normal passenger, the CT gantry is stopped and a projection image of a bag is created. In order to support the high resolution imaging used by a CT scanner during EDS scans, the imaging electronics acquire data significantly faster than today's conventional checkpoint scanners. This increased data acquisition speed allows this embodiment of the invention to speed up the conveyor belt, without sacrificing image quality. Therefore the inspection throughput for normal passenger bags can be more than three times the throughput of a conventional carry-on X-ray system.

In the present embodiment, for CAPPS selectee passengers, the "greeter" helping passengers divest before they place bags on the belt simply indicates to the system (e.g., via a button) that a selectee passenger bag is approaching the system. In a specified period of time, e.g., less than 5 seconds, the CT gantry automatically starts spinning and the EDS system inspects the selectee bag using fully automated EDS techniques. Once the selectee bag is scanned and analyzed, a process that takes a specified time, e.g., approximately 20 seconds, the gantry stops again for normal bag inspection. This entire process can be completely transparent to the passenger. The process described here can eliminate the need for separate screeners for selectee bag hand search.

Figure 19:
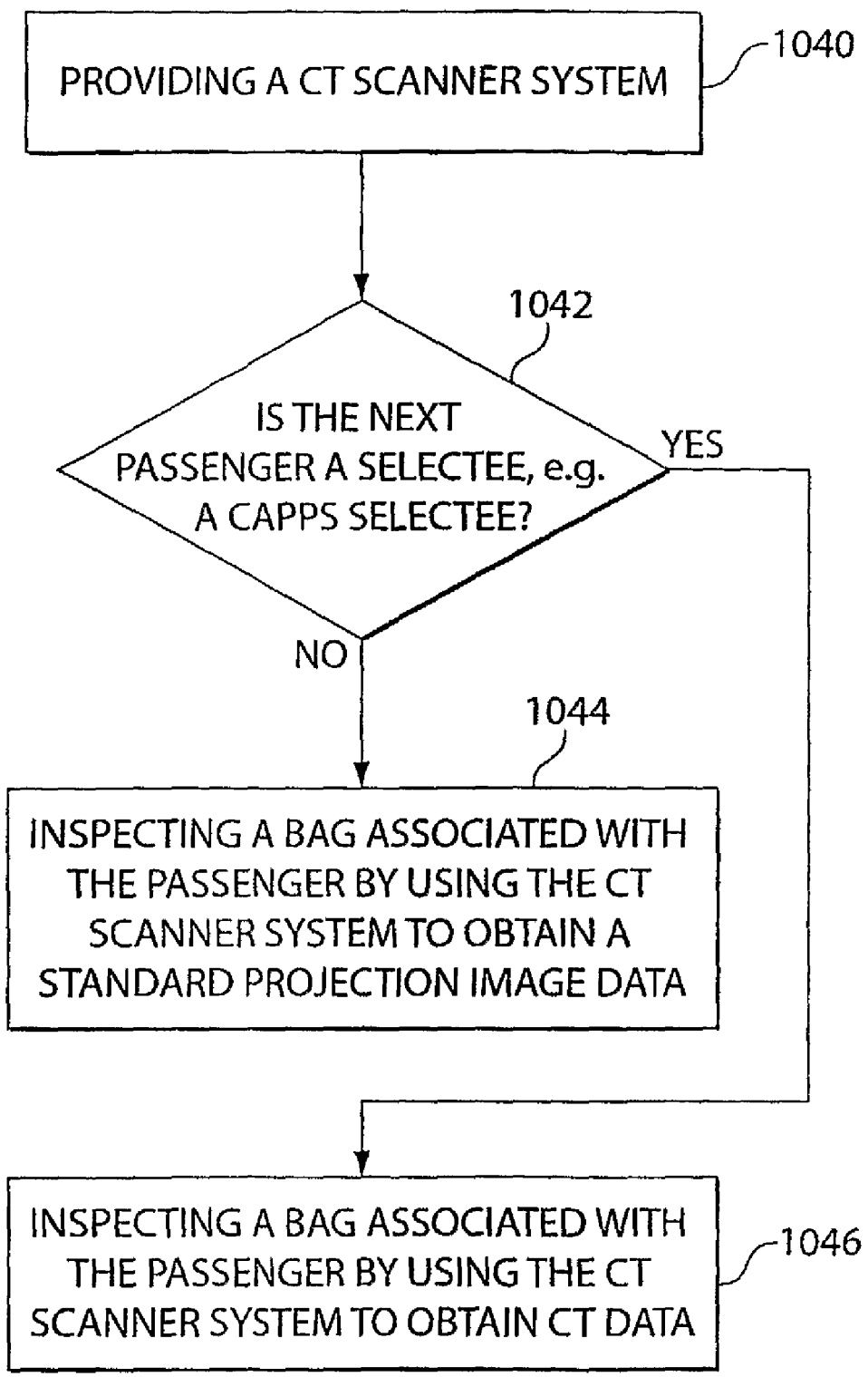
FIG. 19 is a flow chart of a scanning method for achieving high throughput at a carry-on baggage checkpoint using, for example, the embodiment shown in FIG. 3A.

Thus, with reference to FIG. 19, one embodiment of the invention provides a method for scanning a bag to determine if the bag poses a threat. The method includes: providing a CT scanner system; determining if a passenger is a selectee; if the passenger is not a selectee, then inspecting a bag associated with the passenger by using the CT scanner system to obtain a standard projection image data; and if the passenger is a selectee, then inspecting a bag associated with the passenger by using the CT scanner system to obtain CT data. The projection image generated by the CT scanner can be a stationary image or a "twisted" projection scan created using a slowly moving gantry.

In the event of an increase to the national threat level, or increased threat to a specific region or even to a specific airline or flight, one embodiment of a method according to the invention can inspect all bags to the EDS level. This approach will effectively reduce the throughput, e.g., to approximately 150 bags per hour, which is similar to the throughput of today's carry-on inspection machines. Once the threat level is decreased again, the system can be placed back into high throughput mode.

Use of a Visible Light Camera

In another embodiment, the scanner system utilizes a visible light camera to image each bag as it crosses a predetermined point outside or inside the scanner tunnel. The image can then be used by the scanner CPU to automatically identify features of the bag, alter the scan speed to optimize throughput and detection. In another embodiment, the image can be used to associate passenger bags with the scanner data and automated decision. In another embodiment, the visible light image can be used to help a screener identify the location of a suspect object in a passenger's bags.

The present invention has been described with respect to inspection of carry-on baggage, since it has substantial uses in that field. However, the CT scanner system according to the present invention can be used in many other applications for which CT scanners are used. For example, the present invention may also be used in medical CT scanning applications.

Having described at least one embodiment of the invention, modifications, adaptations and improvements will be readily apparent to those of ordinary skill in the art. Such modification, changes and adaptations are considered part of the invention. Accordingly, the foregoing description is by way of example only and is not intended as limiting. The invention's limit is defined only in the following claims and the equivalents thereto.

What is claimed is:

1. A system for detecting a barrel of a weapon in a container, the system comprising:
   a CT scanner operative to perform a CT scan of a container;
   a conveyor for advancing a container through the CT scanner;
   a host processor in communication with the CT scanner and operative to receive CT data from the CT scanner; and
   a detection processor in communication with the host processor and operative to:
   reconstruct slice data;
   analyze the slice data to determine if at least one of a hollow circular shape and an oval shape of a known diameter exists, the shape being surrounded by metal or dense plastic;
   if the shape does not exist, then determine if the detection processor has analyzed the last slice for the container;
   if the detection processor has not analyzed the last slice for the container, then analyzing the next slice to determine if at least one of a hollow circular shape and an oval shape of a known diameter exists, the shape being surrounded by metal or dense plastic; and
   if the detection processor has analyzed the last slice for the container, then determining that no weapon was found in the container.

* * * * *